US008172868B2

(12) United States Patent
Eastman

(10) Patent No.: US 8,172,868 B2
(45) Date of Patent: May 8, 2012

(54) APPARATUS FOR SKIN STIMULATION AND SUBCUTANEOUS TISSUE THERAPY

(76) Inventor: Stephen Bartell Eastman, Scottsdale, AZ (US)

( * ) Notice: Subject to any disclaimer, the term of this patent is extended or adjusted under 35 U.S.C. 154(b) by 518 days.

(21) Appl. No.: 12/163,550

(22) Filed: Jun. 27, 2008

(65) Prior Publication Data

US 2009/0005801 A1    Jan. 1, 2009

Related U.S. Application Data

(60) Provisional application No. 60/946,886, filed on Jun. 28, 2007.

(51) Int. Cl.
 *A61B 17/34* (2006.01)
(52) U.S. Cl. ........................................ 606/186; 606/133
(58) Field of Classification Search .................. 606/186, 606/133, 183; 30/365, 366, 43.8, 43.91, 30/34.1; 604/47, 158, 164.01; D28/50
See application file for complete search history.

(56) References Cited

U.S. PATENT DOCUMENTS

| 3,196,539 | A | * | 7/1965 | Jepson et al. | 30/43.9 |
|---|---|---|---|---|---|
| 5,497,556 | A | * | 3/1996 | Lebessis | 30/365 |
| 5,611,806 | A | | 3/1997 | Jang | |
| 5,964,729 | A | * | 10/1999 | Choi et al. | 604/47 |
| 2005/0288687 | A1 | * | 12/2005 | Dorber et al. | 606/133 |
| 2007/0038181 | A1 | * | 2/2007 | Melamud et al. | 604/158 |

* cited by examiner

*Primary Examiner* — Ryan Severson
*Assistant Examiner* — Tin Nguyen
(74) *Attorney, Agent, or Firm* — Cahill Glazer PLC

(57) ABSTRACT

A device for providing stimulation to the skin and treatment of subcutaneous tissue and methods for using the same. The skin stimulation device comprises a handle affixed to a U-shaped housing having side walls, a cylindrical member inserted into the housing and being rotatable relative to the side walls, a plurality of pins extending in rows outward and a rotatable cover affixed over the housing having slits for the needles such that the rotation of the cover varies the length of the needles extending through the slits. The skin stimulation device can be used to apply therapeutic agents to or below a human skin surface. The rotating cover allows for therapeutic agents to be delivered at a precise depth specified by the user.

5 Claims, 5 Drawing Sheets

APPARATUS FOR SKIN STIMULATION AND SUBCUTANEOUS TISSUE THERAPY

CROSS-REFERENCE TO RELATED APPLICATIONS

This application claims the benefit of U.S. Provisional Application Ser. No. 60/946,886 entitled "METHODS AND APPARATUS FOR SKIN STIMULATION," which was filed on Jun. 28, 2007.

FIELD OF INVENTION

The present invention is directed to a device for providing stimulation to the skin and treatment of subcutaneous tissue. In particular, the present invention is directed to a system for applying needle perforations and pressure to the skin and the like, and specifically, the skin of the face and neck.

BACKGROUND OF THE INVENTION

The present invention is directed to methods and systems related to the application of needles to the skin and particularly needles which are used to puncture the skin of the face and neck.

The skin needs to be treated and nourished below the surface for the most dramatic skin renewal results. The inner surface of the skin should be the target of therapy so as to promote repair from the inside out. The repair process stimulates the production of collagen and leads to faster skin renewal and rejuvenation. Collagen, critical to the renewal process, is the substance that provides skin with its vitality and healthy glow. When the new skin is visible, a process that may take weeks, the new skin is smoother and healthier.

Other methods of promoting skin renewal, such as the use of lasers and dermabrasions, burn the skin. Needle therapy does not. Accordingly, the risk of scarring or hyperpigmentation is lower with needle therapy than its burning alternatives. Needle therapy is not as invasive as said alternatives, so the skin needs less time to recover. It has been shown that the skin can improve 40% to 60% in just one treatment. The procedure can be repeated after six months. As with laser skin treatments, the skin continues to improve for up to a year after the treatment.

The present invention facilitates the production of collagen and elastin, substances that are vital for healthy-looking skin. Before the advent of this device, the only way to apply an active substance was through pills and topically applied chemicals that are generally acidic. The present invention employs fine needles that create small infiltration channels through which creams and exfoliants can reach the dermis directly. The infiltration channels are closed again within minutes after treatment. Relative to a traditional topical preparation, the present invention increases skin penetration by a factor of 40.

The present invention can be further utilized to inject substances subcutaneously. This use enables delivery of therapies targeted to tissue underlying the skin. An exemplary therapy would be the injection of a therapeutic agent into subcutaneous adipose fat tissue, stimulating a reduction in the mass of said tissue. The present invention's dynamic needle infiltration makes this possible, giving the device versatility not found before.

The use of dynamic needle infiltration has several advantages. It is efficient. It is painless. It is compatible with a variety of skin products to achieve a variety of purposes.

There have been several prior systems for needle therapy including commercial tattoo technologies. While there have been several systems directed to needle therapy, there has not been a system in which the effective length of the needles can be adjusted. It is desirable to adjust needle length based upon the patient's skin type, age and skin disease state.

It is an object of an exemplary embodiment of the present invention to provide a needle therapy system which enables the needles to be adjusted.

It is a further object of an exemplary embodiment of the present invention to provide a system which is adjustable and which can be used to treat skin and to facilitate the penetration of various therapeutic agents into and below the skin.

It is a further object of an exemplary embodiment of the present invention to provide a system which can be used for a variety of dermatological applications, including acne prevention, hair growth and exfoliation.

It is a further object of an exemplary embodiment of the present invention to provide a system which can be used to treat a variety of disease states affecting subcutaneous tissue.

These and other objects of the present invention will be described in the detailed description which follows.

SUMMARY OF THE INVENTION

In an exemplary embodiment, the present invention comprises a skin roller that may be used to insert therapeutic agents into variable depths of skin. In accordance with various aspects of an exemplary embodiment, the present invention comprises a skin roller comprising a handle affixed to a U-shaped housing having side walls; a cylindrical member inserted into the housing and being rotatable relative to the side walls, said cylindrical member having a plurality of needles extending perpendicularly in rows outwardly; and a rotatable cover affixed over the U-shaped housing having parallel slits for the plurality of needles such that the rotation of the cover varies the length of the needles extending through the slits. In an exemplary embodiment, the rotatable cover is controlled by an adjustment pin that connects the housing to the cover.

In accordance with various aspects of another exemplary embodiment, the invention is a skin roller comprising a handle affixed to a U-shaped housing having oppositely disposed side walls each having an aligned aperture; a cylindrical member having inserts for insertion into the aligned apertures and being rotatable via the apertures, said cylindrical member having a plurality of undulations about its outer periphery and a plurality of needles extending in rows perpendicularly outward from the undulations; a rotatable cover affixed over the housing and having parallel slits aligned with the rows of needles such that the rotation of the cover varies the length of the needles extending through the slits; and an adjustment pin that connects the rotatable cover to the housing and is capable of fixing the position of the rotatable cover relative to the housing.

BRIEF DESCRIPTION OF THE DRAWINGS

The exemplary embodiments of the present invention will be described in conjunction with the appended drawing figures in which like numerals denote like elements and.

DETAILED DESCRIPTION

The present invention may be described herein in terms of various functional components. It should be appreciated that such functional components may be realized by any number of components to perform the specified functions. In addition, the present invention may be practiced in any number of contexts and the methods and systems described herein are merely exemplary applications of the invention. Further, it should be noted that the present invention may employ any number of conventional techniques for providing stimulation to the skin and treatment of subcutaneous tissue, and such general techniques that may be known to those skilled in the art are not described in detail herein.

In an exemplary embodiment, the invention comprises a dermatological roller mechanism with a plurality of needles which are used to perforate the skin of the user and to provide needed therapy. The inclusion of an adjustable cover with rows of slits that overlay the needles enable the user to adjust the effective length of the needles. The effective length of the needles is the length of the needle that extends past the rotatable cover.

Figure 1:
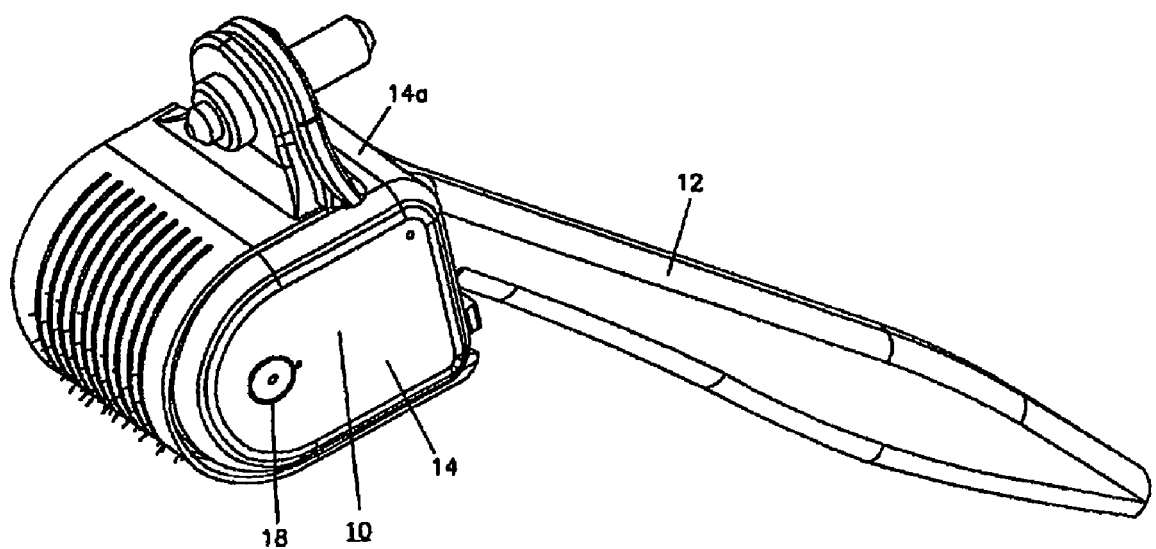
FIG. 1 is an isometric view of a skin stimulation device in accordance with an exemplary embodiment of the present invention.
Figure 2:
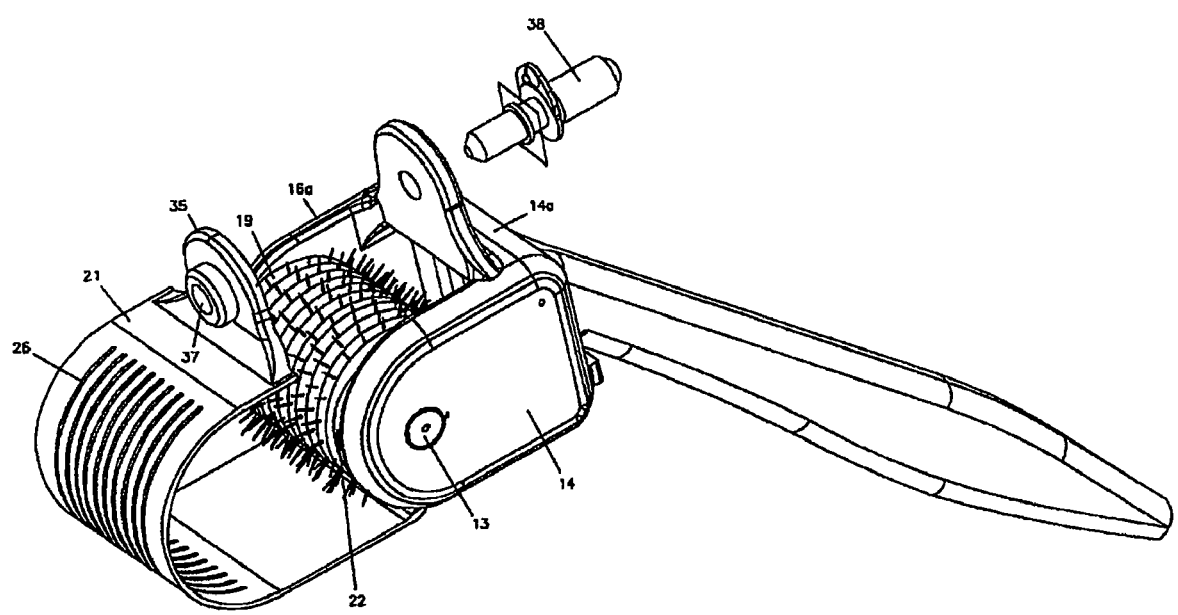
FIG. 2 is an exploded view of a skin stimulation device in accordance with an exemplary embodiment of the present invention.
Figure 3:
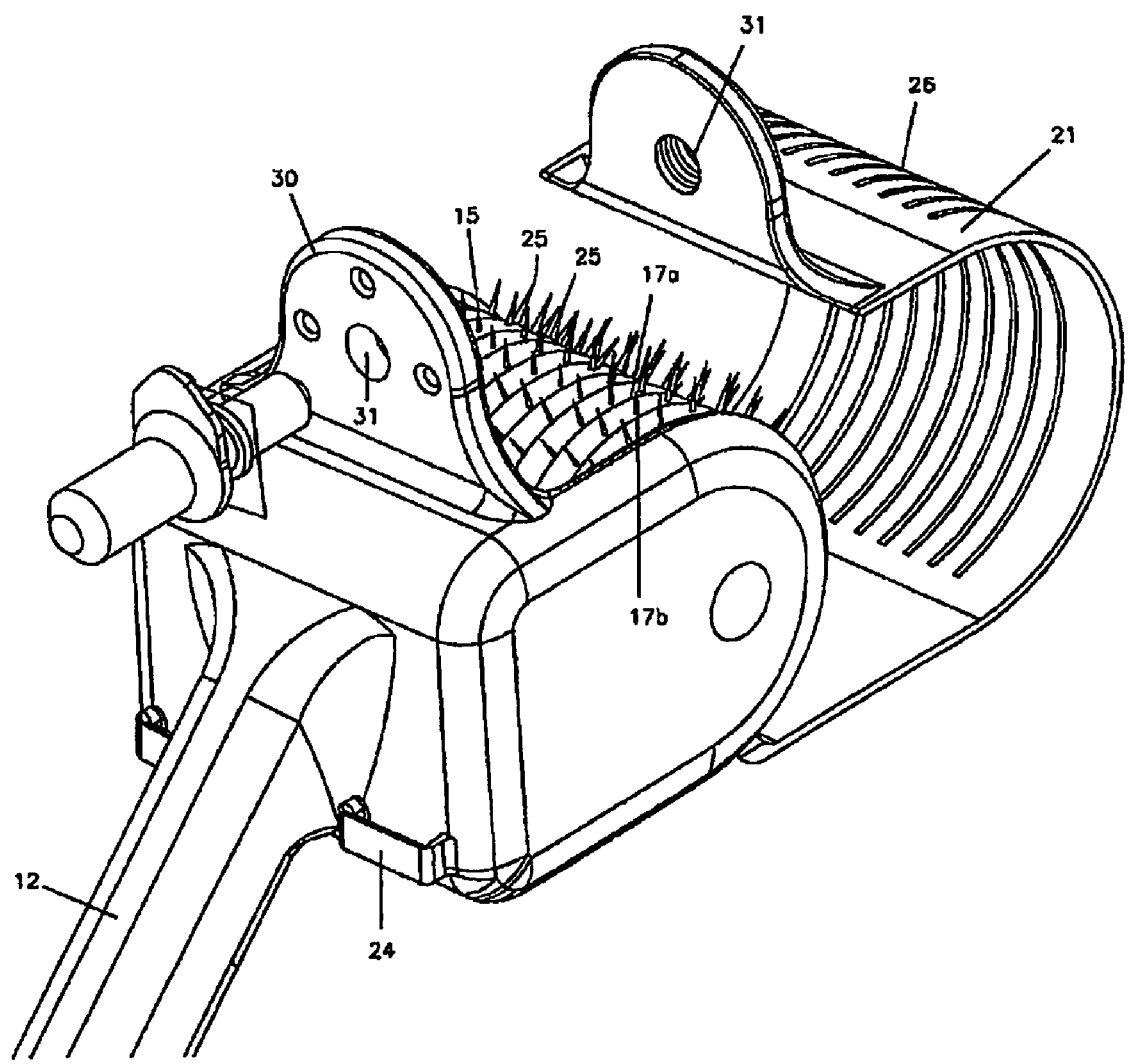
FIG. 3 is an exploded view of a skin stimulation device in accordance with an exemplary embodiment of the present invention.
Figure 4:
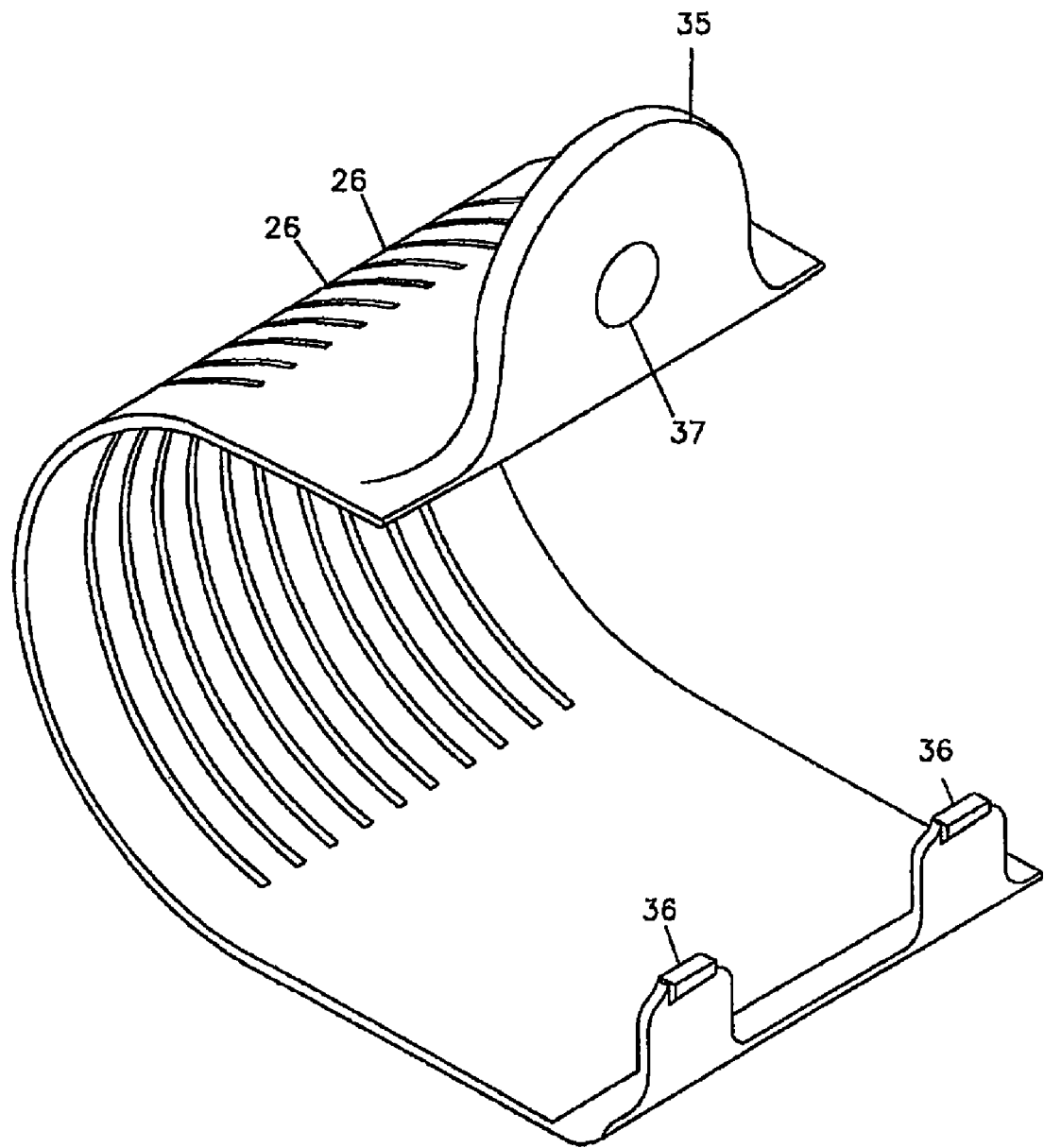
FIG. 4 is an isolated view of a rotatable cover in accordance with an exemplary embodiment of the present invention.
Figure 5:
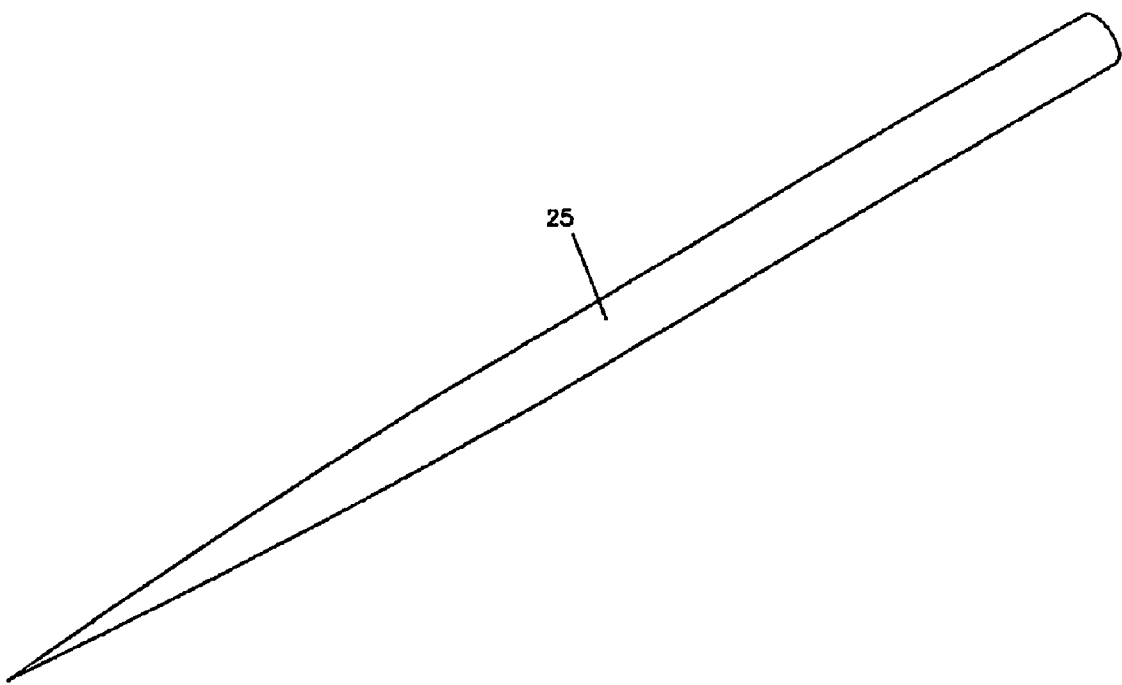
FIG. 5 is an isolated view of a needle in accordance with an exemplary embodiment of the invention.

Referring to FIGS. 1 to 5, in accordance with exemplary embodiments, the present invention comprises an adjustable system for enabling users to perforate the skin using needles. The invention, in one embodiment, comprises a needling member 10 attached to a handle 12. Needling member 10, in one embodiment, is a multi-piece system which may be constructed from a variety of materials such as plastic or metal.

The system comprises a U-shaped housing 14, the rear 14a of which is affixed to handle 12. U-shaped housing 14 has two opposing side walls 16a with aligned bores or apertures 18 and a flap 30 which extends upward with an aperture 31. U-shaped housing 14 may be constructed from a variety of materials such as plastic or metal.

In an exemplary embodiment, the invention includes a cylindrical barrel 15 having coaxial extensions 13, which insert into bores 18, and thus permits barrel 15 to rotate. Cylindrical barrel 15 has a plurality of coaxial undulations 19 about its outer periphery which comprise a plurality of peaks 17a and valleys 17b. Within valleys 17b are embedded parallel rows of needles 25 which extend perpendicularly outward from barrel 15 and which are used to pierce the skin of the user when in use. The needles may be constructed of any material that is suitable for penetrating the skin. In some embodiments, the needles may be solid. In other embodiments, the needles may have a hollow interior chamber for facilitating the application of therapeutic agents.

In an exemplary embodiment, the present invention has a U-shaped cover 21 which fits over and mates with U-shaped housing 14. In accordance with various aspects of an exemplary embodiment, U-shaped cover 21 has a plurality of parallel slits 26 which extend along its length and align with the rows of needles 25 on barrel 15, such that parallel rows of needles 25 extend outward through parallel rows of slits 26. The cover may be constructed from a variety of materials such as plastic or metal.

U-shaped cover member 21 is pivotably attached to the rear of the housing via a catch 24 and tabs 36. Cover member 21 can thus pivot inward and outward with respect to barrel 15, and can be used to adjust the effective length of needles 25 extending through slits 26. The opposing end of the cover has a flap 35 with an aperture 37 with aligns with flap 30 and aperture 31 of U-shaped housing 14.

In an exemplary embodiment, the invention includes an adjustment mechanism comprising an adjustable pin 38, which is inserted into aligned apertures 31, 37. Pin 38 has a plurality of positions which pivotably move cover member 21 toward or away from the back piece of housing 14. In this way the effective length of needles 25 extending outside cover 21 can be varied.

In an exemplary embodiment, this invention includes methods for skin and underlying tissue treatment or therapy using the adjustable system described herein, and in FIGS. 1 to 5 to bring about various health and/or cosmetic benefits. For example, the system may be effective by itself, or as a complement to standard care, in treating nausea, pain, addiction, inflammation, excess adipose tissue, osteoarthritis, or asthma.

This invention also includes methods for treating the skin and underlying tissue using a kit comprising the adjustable system described herein and a therapeutic agent. The adjustable system perforates the skin to the desired depth, delivers the therapeutic agent to the desired tissue, and thereby facilitates the penetration of the therapeutic agent for a desired treatment or therapy.

While any therapeutic agent is appropriate for use with the present invention, exemplary therapeutic agents may comprise one or more of a fat treatment agent (e.g., phosphatidylcholine deoxycholate), muscle relaxant (e.g., Botulinum toxin (Botox®)), anti-inflammatory agent (e.g., cortisone), filler, moisturizer, anesthetic, vitamin, mineral, hormone, medicinal agent, or tanning agent.

It will be understood that the foregoing description is of exemplary embodiments of the invention, and that the invention is not limited to the specific forms shown. Various modifications may be made in the design and arrangement of the elements set forth herein without departing from the scope of the invention. These and other changes or modifications are intended to be included within the scope of the present invention. The true nature and scope of the present invention is to be determined with reference to the attached claims.

I claim:

1. A skin stimulation device comprising:
   a handle;
   a housing having a plurality of side walls, said housing being in physical communication with said handle;
   a cylindrical member having an outer surface and having an axis of rotation, said cylindrical member being in physical communication with said housing and being configured such that said cylindrical member may rotate about its axis relative to said plurality of side walls;
   a plurality of needles secured to, and extending radially outward from, the outer surface of said cylindrical member;
   a rotatable cover having a plurality of parallel slits, said rotatable cover being pivotally secured to the housing for movement relative thereto, such that said plurality of needles extend through said plurality of parallel slits and rotate relative to said rotatable cover while said skin stimulation device is in use, said rotatable cover being configured such that movement of said rotatable cover relative to said housing varies the exposed length of the plurality of needles extending through said plurality of parallel slits; and an adjustment mechanism in physical communication with said rotatable cover and said housing, said adjustment mechanism fixing the position of said rotatable cover relative to said housing.

2. The skin stimulation device of claim 1, wherein said adjustment mechanism is an adjustment pin configured to move the position of said rotatable cover relative to said housing.

3. The skin stimulation device recited by claim 1, wherein said housing is U-shaped.

4. A skin stimulation device comprising:
a handle;
a housing having two oppositely disposed side walls;
a cylindrical member having an outer surface, said cylindrical member having opposing first and second ends rotatably supported by said side walls of said housing for allowing said cylindrical member to rotate about an axis relative to said housing;
a plurality of needles configured to extend radially outward from the outer surface of said cylindrical member;
a rotatable cover having a plurality of parallel slits pivotally secured to said housing for movement relative thereto such that said plurality of needles extend through said plurality of parallel slits and rotate relative to said rotatable cover while said skin stimulation device is in use, said rotatable cover being configured such that movement of said rotatable cover relative to said housing varies the exposed length of the plurality of needles extending through said plurality of parallel slits; and
an adjustment pin being in physical communication with said rotatable cover and said housing, said adjustment pin being configured to move the position of said rotatable cover relative to said housing.

5. The skin stimulation device recited by claim 4, wherein said housing is U-shaped.

* * * * *